United States Patent [19]

Chou

[11] Patent Number: 4,966,731
[45] Date of Patent: Oct. 30, 1990

[54] PROCESS FOR PREPARING SULFONYL ACIDS

[75] Inventor: Yueting Chou, Chesterfield, Mo.

[73] Assignee: Monsanto Company, St. Louis, Mo.

[21] Appl. No.: 464,262

[22] Filed: Jan. 12, 1990

[51] Int. Cl.$^5$ .................... C11C 1/00; C07C 315/00
[52] U.S. Cl. .................... 260/400; 260/402; 560/11; 562/429
[58] Field of Search ............ 562/429; 260/400, 402

[56] References Cited

U.S. PATENT DOCUMENTS

| 2,603,658 | 7/1952 | Hanusch | 562/429 |
| 2,969,387 | 1/1961 | Horn et al. | 560/11 X |
| 4,758,369 | 7/1988 | Dyroff et al. | 252/94 |
| 4,824,591 | 4/1989 | Dyroff et al. | 252/94 |

OTHER PUBLICATIONS

Node et al, JOC (1961), vol. 46, pp. 5163–5172.
S. S. Kukalenko, Zhur., Organicheskoi Khimii, 6, No. 4, (English translation), pp. 680–684, Apr. 1970.
Kresze et al, *Jahrg.* 94, pp. 2060–2072, Jan. 25, 1961.
*"Acetylene and Carbon Monoxide Chemistry"*, John W. Copenhaver & Maurice H. Bigelow, Copyright (1949), pp. 156–157.
Rapoport et al, *JACS* 69, pp. 693–694, Oct. 7, 1946.

*Primary Examiner*—Werren B. Lone
*Assistant Examiner*—Vera C. Clarke
*Attorney, Agent, or Firm*—R. C. Loyer

[57] ABSTRACT

There is disclosed a process for preparing sulfonyl acids from mercaptans in a single reactor. The mercaptan is converted to mercaptide and reacted with a lactone or lactam in an organic solvent which is removed after formation of a thioether containing acid. Water is provided as a solvent for the oxidation of the thioether to the sulfone. Mild conditions and readily available starting materials render the method capable of preparing such acids in large scale amounts.

12 Claims, No Drawings

PROCESS FOR PREPARING SULFONYL ACIDS

This invention relates to a process for preparing organic acids containing a sulfonyl group and more particularly to a process for preparing such materials from a lactone or lactam.

BACKGROUND OF THE INVENTION

Lactones have been employed in the prior art to produce alkylsulfonyl acids. However, the processes employed were either difficult to operate or relied upon scarce starting materials. Processes for the convenient production of sulfonyl acids and in particular alkylsulfonylbutric acids, have not been available. γ-butyrolactone has been employed in several different processes whereby the lactone ring is opened and either a sulfide or sulfonyl acid is prepared. In the case of the sulfide, the acid is oxidized to the sulfonyl form.

An example of such use of the lactone ring opening method is found in U.S. Pat. No. 2,603,658 to Hanusch which discloses a reaction of γ-butuyrolactone and the sodium salt of benzene sulfonic acid to prepare the sodium salt of phenylsulfonyl butyric acid. The lactone was disclosed as not only the reactant in the process but also as a solvent when employed in excess. The free acid was obtained by dissolving the reaction product in water and reprecipitating it with mineral acids. While sulfonic acids are known these materials are not generally available.

Thioethers have been produced by ring opening reactions employing lactones with a Lewis acid such as aluminum halide. The thioethers is formed by reacting a thiol with the lactone. Several lactones are reported to have been employed while both alkane and aryl thiol compounds were found to be useful in this process. Such a process is described by Node et al in J.O.C. pp 5163–5166, Vol. 46, (1981). While the thioethers were reported to have been prepared there was no suggestion to further react the thioethers to provide the sulfonyl containing organic acid.

In an entirely different process, lactone ring opening has been described by reactions of mercaptans with lactones in the presence of sodium metal. One example of such a reaction is disclosed by S. S. Kukalenko, Zhur. Organ. Khimii, Vol. 6, No. 4, pp. 682–685 (1970). According to this publication, a mixture of thiophenol, alcohol and either metallic sodium or potassium reacts in the solvent with butyrolactone to provide an aryl thiobutyric acid which was oxidized to a sulfonyl acid. A similar process is also disclosed by Kresze et al Chem. Ber. 94 pp. 2060–2072 (1961). This publication also discloses the reaction of γ-butyrolactone with a thiophenol in methanol and in the presence of sodium. A thioether is produced.

However, processes have been known whereby alkylsulfonyl acids are provided by oxidations of a corresponding acid containing a thioether group. Symmetrical diacids are prepared from butyrolactone and sodium sulfide. Butyrolactone was employed as a reactant and a solvent in the reaction provide the thioether containing acid. The thioether was then oxidized to the sulfone dibutyric acid with an oxidizing agent. For large scale production it was suggested that chlorination in aqueous solution be employed to convert the thioether to the sulfone. Oxidation of the crude thioether reaction product dissolved in water was also disclosed. Of course, by this process only symmetrical diacids could be prepared. A disclosure of such a process is found in Acetylene and Carbon Monoxide Chemistry, pp. 156 and 157.

Other processes for preparing sulfonylacids is described in U.S. Pat. No. 2,969,387 to Horn et al. Severe reaction conditions are required to prepare a di (sulfonylalkanoate). According to this procedure butanedithiol is dissolved in aqueous ethanol containing sodium hydroxide. After the mercaptide is formed, butyrolactone is added slowly at a temperature of from 190–210° C. Heating at this high temperature proceeded for 24 hours. The product was then filtered and dissolved in water and acidified to produce a dithiol dibutyric acid. To form the sulfonyl acid, the dithiol dibutryic acid is dissolved in water containing sodium hydroxide and treated with peracetic acid, while maintaining the pH of the reaction in the range of from 6 to 7 by addition of sodium hydroxide. After addition was completed, the sulfonyl acid was recovered. While this process accomplishes the production of a sulfonyl acid, the reaction conditions are severe and extended. Also, because of the severe conditions, a high boiling solvent such as dibutyl carbitol was employed in the reaction with the lactone and low yields, in the order of 50%, is reported.

Several different approaches to prepare sulfonyl acids is reported by Rapoport et al, JACS 69, 693 and 694 (1947). Three general methods are described to provide alkylmercapto acids which are (1) the condensation of a mercaptan with the appropriate halo-acid, halo-ester, or halo-nitride, followed by hydrolysis where necessary; (2) the alkylation of a ω-mercapto acid with an alkyl iodide; and (3) the addition of a mercaptan to acrylonitirile followed by acid hydrolysis of the resultant nitrile. Oxidation of the thioether with hydrogen peroxide provide the alkysulfonyl acid. Severe reaction conditions and long reaction times are reported.

There has recently been discovered novel sulfone mono-peroxy and diperoxy acids exhibiting extra ordinary stability and attractive properties for use as bleach for laundry detergent use. Examples of such sulfone peroxy acids are found in U.S. Pat. Nos. 4,758,369 and 4,824,591. The sulfone peroxy acids have exhibited such unusually favorable properties as bleaches for detergent use in home laundry detergents. Production in large volume to supply such need has not been heretofor available. There is thus needed a convenient, efficient and safe process for preparing sulfonyl acids, the precursors for sulfone peroxy acids.

BRIEF DESCRIPTION OF THE INVENTION

In accordance with this invention there is provided a process for the preparation of sulfonyl peroxy acids in situ by chlorine oxidation of a thioether intermediate which was prepared from a mercaptan, sodium hydroxide and a lactone or lactam ring compound.

In accordance with this invention there is provided a process for the preparation of sulfonyl acids which are, because of the purity, and ease of preparation, readily oxidized to the peracid state for use in laundry bleach compositions. The inventive process provides five steps in situ. In the first step a sodium mercaptide is formed by the reaction of a mercaptan and sodium hydroxide in an organic solvent. After this reaction, the water formed by such reaction is removed from the reactor by azeotropic distillation with a portion of the solvent. In the third step a ring compound such as γ-butyrolactone (GBL), is added with additional solvent if required. Sufficient energy is added to cause a ring opening reaction producing a thioether. After formation of the thioether the organic solvent is removed from the reactor such as by distillation and water added. The thioether dissolves in the water and is conveniently oxidized by chlorine gas to provide a sulfonyl acid, which precipitates from the aqueous media.

The sulfonyl acid is conveniently recovered by filtration.

The process may be briefly described by the following reactions (1) RSH + NaOH = RSNa + H₂O

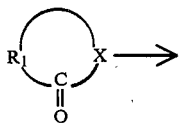

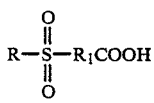

wherein R is selected from the group consisting of alkyl radicals having from 1 to 20 carbon atoms, aryl, alkyaryl, aralkyl, and cycloalkyl radials having from 4 to 9 carbon atoms, R1 is a ring closing moeity and X is selected from the group consisting of nitrogen and oxygen.

DETAILED DESCRIPTION OF THE INVENTION

In accordance with this invention, there is provided a process wherein mild conditions are employed and a single reactor for all steps is provided. Because of this simplification, sulfonyl acids are provided economically and in such high yield that large scale production is possible.

In the first step, a mercaptide is formed by the reaction of a mercaptan with an appropriate alkali metal, such as sodium or potassium. The alkali metal employed may be in the solid form, although highly concentrated solutions, such as the hydroxide, may be employed. However, the introduction of aqueous solutions of the alkali metal hydroxide generally reduces the yield in the reaction. It is preferred that the formation of the mercaptide be undertaken with the minimum amount of water, beginning with an anhydrous condition. To avoid the difficulty of working with metallic sodium, it has been found that sodium hydroxide pellets may be employed to form the mercaptide by the reaction with an appropriate mercaptan. The reaction is carried out in the presence of a suitable organic solvent.

Suitable solvents are those which maintain the mercaptan in solution and which will azeotrope water after completion of the reaction when water is generated. Such solvent may be either miscible or immiscible with water, but should not interfere with the reaction or be reactive with any of the contents of the reactor. The amount of solvent employed in the formation of the mercaptide is not critical but is preferred to be in the range of from about 4 to about 6 volumes of solvent for each volume of mercaptan. High volume ratios result in reduced yield and purity of product. Lower volume ratios will not efficiently dissolve the alkali metal hydroxide, when employed to provide the alkali metal. Suitable solvents include low molecular weight alcohols having from 1 to 6 carbon atoms such as methanol, ethanol, propanol, and preferably, butanol, although higher molecular weight alcohols such as hexanol and octanol may also be employed. Other typical organic solvents include toluene, xylene or mercaptan reactant. Alcohol is the preferred solvent.

After completion of the reaction of the mercaptan with the alkali metal hydroxide, water is removed by azeotropic distillation, whereby the solvent employed for the reaction is distilled, carrying with it the water produced during the mercaptide formation. For this purpose, excess solvent is employed in the mercaptide reaction to allow for removal of the water. Of course, if the alkali metal is employed in the metallic forms no water is produced and its removal obviated.

After removal of the water, a suitable lactone or lactam is added to the reactor, together with optional amounts of solvent depending on the solvent loss during water removal. Typically, about one-third of the organic solvent is lost during water removal. The lactones have been found to react quantitatively with the mercaptide to produce a thioether in a ring opening process. Generally, temperatures in the range of from about 100° C. to about 150° C. provides adequate reaction rate, while temperatures in the range from about 110° C. to about 120° C. provides quantitative reaction in about one-hour. A slight excess of the lactone may be employed to react with unreacted sodium from the first step to form the sodium salt of the acid corresponding to the lactone.

Examples of ring compounds include, but are not limited to γ-butyrolactone, γ-valerolactone, δ-valerolactone, γ-caparolactone, β-propiolactone, β-butyrolactone, β-isobutyrolactone, γ-octanoiclactone, ε-caprolactone, γ-nonanoiclactone, decanoiclactone, and the nitrogen analogs of the above named compounds such as ε-caprolactam and γ-valerolactam.

The organic solvent is removed from the reactor after the thioether preparation. When using relatively low molecular weight alcohols, the solvent may be removed by distillation. It has been found that the major portion of the solvent can be removed by distillation without further purification while the remaining amount, in the range of about 15% of the total, is removed by steam distillation. It is essential that the solvent be removed from the reactor to avoid impurities in the final product. After stripping the organic solvent from the reactor, water is added to the reactor preparing the intermediate thio compound for oxidation.

It has been found that the thioether prepared in accordance with the process of this invention is easily oxidized by chlorine oxidation. Yields as high as 98% have been obtained. Generally, the oxidation is accomplished by passing chlorine gas through the water in the reactor. The reactor is maintained at a temperature in the range of from about 40° C. to about 60° C. Since the oxidation reaction is exothermic, cooling of the reactor is required to maintain the temperature in the desired range. Any unreacted mercaptan remaining in the reactor from the first step is oxidized to the sulfonyl chloride, or possibly to the corresponding sulfonic acid. The desired sulfonyl acid is easily recovered by filtration and purified by reslurrying with water to remove most of the impurities. To provide high purity product, recrystallization from an organic solvent may be performed.

The invention Will be best understood by the following example which illustrates, but which does not limit the practice and effectiveness of the process of this invention.

EXAMPLE 1

To a 500 cc, 4-neck, round-bottomed flask equipped with a 10-tray Oldershaw distillation column and an overhead mechanical stirrer was charged 4.16g (0.104 mole) NaOH pellets, 14.6g (0.10 mole) octylmercaptan and 59.5g butanol. The mixture was stirred and heated to reflux. After all the NaOH had been dissolved, about 20–22 cc butanol/water distillate was collected. Time used in the mercaptide preparation step was less than 50 minutes. At 123° C., 9.1g (0.105 mole) γ-butyrolactone was added to the system in one minute. The reaction was run at 115° C. for ½ hour and butanol was stripped. When the flow of the distillate nearly stopped, 190 cc water was added to the system slowly. The distillation was continued until no more butanol was present in the overhead. Then, 70cc of cold water was added to the mixture to lower the mixture temperature. At 50° C., chlorine gas was bubbled through the vigorously agitated solution. The off gas was scrubbed with NaOH solution. The oxidation was maintained around 50° C. and was completed in 3–5 minutes. Nevertheless, an additional 15 minutes was allowed with a lower chlorine flow rate. A white slurry was formed, cooled and filtered. The filter cake was reslurried with water twice. The wet cake was transferred to a dish and air-dried at room temperature. 25.2g of the dry product was obtained (95.3%) yield, which was not including the leak lost during the distillation). HPLC analysis showed it was about 90.4% pure octylsulfonylbutyric acid.

I claim:

1. A process for the preparation of sulfonylacids represented by the formula:

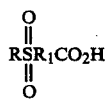

wherein R is selected from the group consisting of alkyl radicals having from 1 to 20 carbon atoms, cycloalkyl radicals having from 4 to 9 carbon atoms, aryl, and alkyaryl radicals and $R_1$ is an alkylene radical having from 3 to 10 carbons, which comprises performing the following steps in a single reactor:

(a) reacting an alkali metal or hydroxide with a mercaptan represented by the formula:

RSH wherein R is as defined above, in an organic solvent for said mercaptan, whereby an alkali metal mercaptide is formed, (b) removing any water formed by the reaction of (a) above from the reactor by azeotropic distillation with said solvent, (c) adding to the reactor a lactone or lactam represented by the formula:

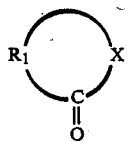

wherein $R_1$ is as defined above, X is selected from the group consisting of nitrogen and oxygen, reacting said lactone or lactam with the mercaptide to form a thioether, removing the organic solvent from the reactor by distillation and adding water to dissolve the reaction product, oxidizing the thiether to form a sulfonyl containing acid by chlorine oxidation.

2. The process of claim 1 further including the step of adding additional solvent together with the lactone or lactam in step c.

3. The process of claim 1 wherein the lactone is gamma-butyrolactone.

4. The process of claim 3 wherein the mercaptan is octylmercaptan.

5. The process of claim 4 wherein the alkali metal is sodium in the form of sodium hydroxide pellets.

6. The process of claim 4 wherein the organic solvent is a low molecular weight alcohol.

7. The process of claim 6 wherein the organic solvent is butanol.

8. The process of claim 1 wherein the mercaptan is phenylmercaptan.

9. The process of claim 1 wherein the alkali metal is sodium in the metallic form.

10. The process of claim 4 wherein the step c is conducted at a temperature of from about 110° C. to about 120° C.

11. The process of claim 1 wherein the mercaptide is reacted with a lactone.

12. The process of claim 1 wherein the mercaptide is reacted with a lactam.

* * * * *

UNITED STATES PATENT AND TRADEMARK OFFICE
CERTIFICATE OF CORRECTION

PATENT NO. : 4,966,731
DATED : October 30, 1990
INVENTOR(S) : Yueting Chou

It is certified that error appears in the above-identified patent and that said Letters Patent is hereby corrected as shown below:

Column 3, lines 11-23 should read as follows:

(1)　　RSH + NaOH $\rightleftharpoons$　　RSNa + $H_2O$ (2)　　RSNa + 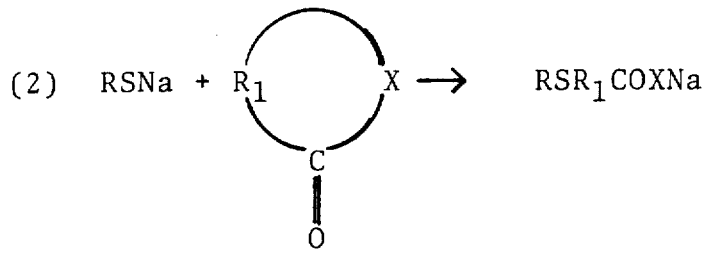 RSR$_1$COXNa (3)　　RSR$_1$COXNa + $3H_2O$ + $2Cl_2$ $\rightarrow$

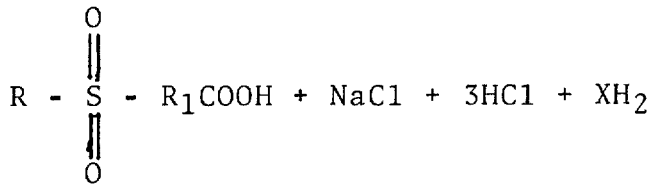 R$_1$COOH + NaCl + 3HCl + XH$_2$

Signed and Sealed this

Eighteenth Day of February, 1992

*Attest:*

HARRY F. MANBECK, JR.

*Attesting Officer*　　*Commissioner of Patents and Trademarks*